United States Patent
Tchaicheeyan et al.

(10) Patent No.: US 10,120,298 B2
(45) Date of Patent: Nov. 6, 2018

(54) MANUFACTURE OF A CHARGE DIRECTOR

(71) Applicant: HP Indigo B.V., Amstelveen (NL)

(72) Inventors: Hanit Marom Tchaicheeyan, Ness Ziona (IL); Eyal Bachar, Ness Ziona (IL); Julia Kornilov, Ness Ziona (IL); Albert Teishev, Ness Ziona (IL)

(73) Assignee: HP Indigo B.V., Amstelveen (NL)

( * ) Notice: Subject to any disclaimer, the term of this patent is extended or adjusted under 35 U.S.C. 154(b) by 0 days.

(21) Appl. No.: 15/547,772

(22) PCT Filed: Apr. 2, 2015

(86) PCT No.: PCT/EP2015/057398
§ 371 (c)(1),
(2) Date: Jul. 31, 2017

(87) PCT Pub. No.: WO2016/155842
PCT Pub. Date: Oct. 6, 2016

(65) Prior Publication Data
US 2018/0024456 A1    Jan. 25, 2018

(51) Int. Cl.
| | |
|---|---|
| G03G 9/135 | (2006.01) |
| C01B 25/32 | (2006.01) |
| C07C 29/68 | (2006.01) |
| C07C 303/32 | (2006.01) |
| C07C 303/44 | (2006.01) |
| C07C 309/17 | (2006.01) |

(52) U.S. Cl.
CPC ........... *G03G 9/135* (2013.01); *C01B 25/322* (2013.01); *C01B 25/324* (2013.01); *C07C 29/685* (2013.01); *C07C 303/32* (2013.01); *C07C 303/44* (2013.01); *C07C 309/17* (2013.01); *C01B 25/32* (2013.01)

(58) Field of Classification Search
None
See application file for complete search history.

(56) References Cited

U.S. PATENT DOCUMENTS

| | | |
|---|---|---|
| 5,304,451 A | 4/1994 | Felder et al. |
| 5,840,453 A | 11/1998 | Swidler |
| 6,136,493 A | 10/2000 | Fujiwara et al. |
| 6,905,807 B2 | 6/2005 | Morrison et al. |
| 7,074,537 B2 | 7/2006 | Qian et al. |
| 8,846,288 B2 | 9/2014 | Ochiai et al. |
| 2011/0266347 A1 | 11/2011 | Grinwald et al. |
| 2012/0018683 A1 | 1/2012 | Almog et al. |

(Continued)

OTHER PUBLICATIONS 12230-71-6 (Alfa Aesar product sheet for barium hydroxide octahydrate, p. 1-2, downloaded from https://www.alfa.com/en/catalog/A12714/ on Jan. 19, 2018).*

(Continued)

*Primary Examiner* — Jafar F Parsa
*Assistant Examiner* — Amy C Bonaparte
(74) *Attorney, Agent, or Firm* — Thorpe North & Western LLP

(57) ABSTRACT

Herein is described a method for the manufacture of a charge director comprising a barium salt. The method comprises reacting barium alkoxide with an acid in a reaction medium comprising ethanol, and separating ethanol from the reaction mixture to recover the barium salt produced.

17 Claims, 3 Drawing Sheets

(56) References Cited

U.S. PATENT DOCUMENTS

2014/0314449 A1 10/2014 Roditi et al.

OTHER PUBLICATIONS 24363-37-9 (Alfa Aesar product sheet for barium isopropoxide, p. 1-2, downloaded from https://www.alfa.com/en/catalog/041338/ on Jan. 19, 2018).*
Leonard ("chapter ten: Working up the reaction" Advanced Practical Organic Chemistry, p. 191-208, 2010).*
International Search Report and Written Opinion dated Dec. 2, 2015 for PCT/EP2015/057398; Applicant Hewlett-Packard Indigo B.V.

* cited by examiner

MANUFACTURE OF A CHARGE DIRECTOR

BACKGROUND

Electrostatic or electrophotographic printing processes typically involve creating an image on a photoconductive surface, applying an ink having charged particles to the photoconductive surface, such that they selectively bind to the image, and then transferring the charged particles in the form of the image to a print substrate.

The photoconductive surface is typically on a cylinder and is often termed a photo imaging plate (PIP). The photoconductive surface is selectively charged with a latent electrostatic image having image and background areas with different potentials. For example, an electrostatic ink composition comprising charged toner particles in a carrier liquid can be brought into contact with the selectively charged photoconductive surface. The charged toner particles adhere to the image areas of the latent image while the background areas remain clean. The image is then transferred to a print substrate (e.g. paper) directly or, more commonly, by being first transferred to an intermediate transfer member, which can be a soft swelling blanket, and then to the print substrate.

Typically the electrostatic ink composition comprises a thermoplastic resin or polymer as the basis for the toner particles (also referred to herein as ink particles), and a non-polar liquid as a carrier liquid in which the toner particles are dispersed. Generally, the toner particles contain a colorant such as a pigment. A charge director, also called charge control agent or imaging agent, is also added to the dispersion to induce charge on the particles. As known in the art, a charge adjuvant may be added to increase the charging effect of the charge director.

DETAILED DESCRIPTION

Figure 1:
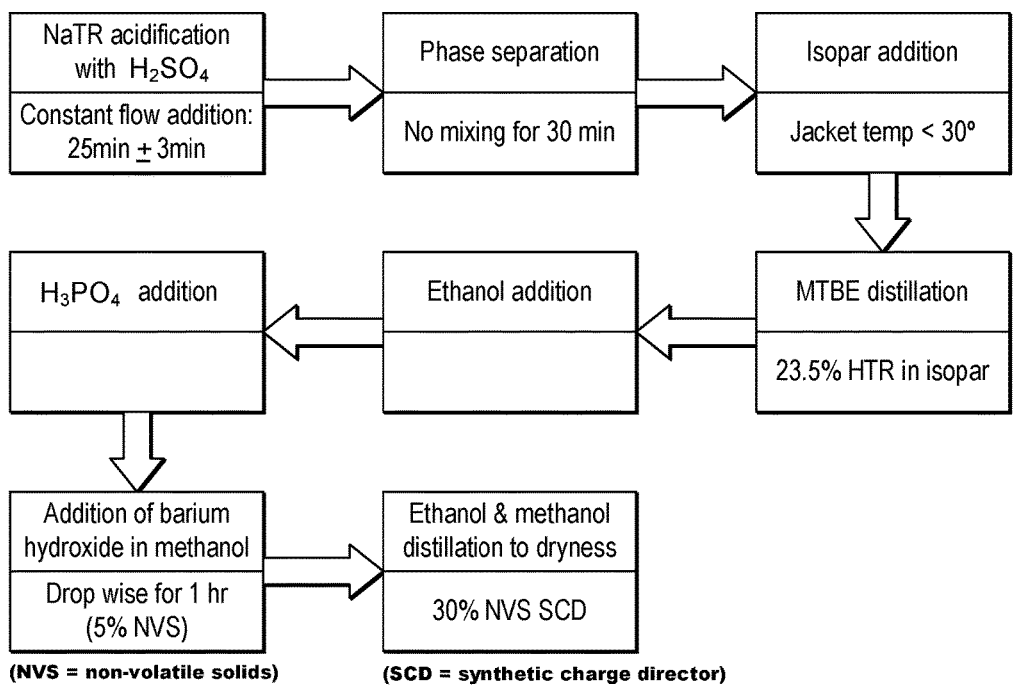
FIG. 1 is a schematic flow diagram of the method described in Comparative Example 1

Before the present disclosure is disclosed and described, it is to be understood that this disclosure is not limited to the particular process steps and materials disclosed herein because such process steps and materials may vary somewhat. It is also to be understood that the terminology used herein is used for the purpose of describing particular examples. The terms are not intended to be limiting because the scope is intended to be limited by the appended claims and equivalents thereof.

It is noted that, as used in this specification and the appended claims, the singular forms "a," "an," and "the" include plural referents unless the context clearly dictates otherwise.

As used herein, "carrier fluid", "carrier liquid," "carrier," or "carrier vehicle" refers to the fluid in which the polymers, particles, colorant, charge directors and other additives can be dispersed to form a liquid electrostatic composition or electrophotographic composition. The carrier liquids may include a mixture of a variety of different agents, such as surfactants, co-solvents, viscosity modifiers, and/or other possible ingredients.

As used herein, "liquid electrophotographic composition" generally refers to a composition, which may be in liquid or powder form, that is typically suitable for use in an electrophotographic printing process and which is free from pigment. The liquid electrophotographic composition may comprise chargeable particles of a resin, which may be as described herein, dispersed in a carrier liquid, which may be as described herein.

As used herein, "co-polymer" refers to a polymer that is polymerized from at least two monomers.

As used herein, "melt flow rate" generally refers to the extrusion rate of a resin through an orifice of defined dimensions at a specified temperature and load, usually reported as temperature/load, e.g. 190° C./2.16 kg. Flow rates can be used to differentiate grades or provide a measure of degradation of a material as a result of molding. In the present disclosure, "melt flow rate" is measured per ASTM D1238-04c Standard Test Method for Melt Flow Rates of Thermoplastics by Extrusion Plastometer, as known in the art. If a melt flow rate of a particular polymer is specified, unless otherwise stated, it is the melt flow rate for that polymer alone, in the absence of any of the other components of the electrostatic composition.

As used herein, "acidity," "acid number," or "acid value" refers to the mass of potassium hydroxide (KOH) in milligrams that neutralizes one gram of a substance. The acidity of a polymer can be measured according to standard techniques, for example as described in ASTM D1386. If the acidity of a particular polymer is specified, unless otherwise stated, it is the acidity for that polymer alone, in the absence of any of the other components of the liquid toner composition.

As used herein, "melt viscosity" generally refers to the ratio of shear stress to shear rate at a given shear stress or shear rate. Testing is generally performed using a capillary rheometer. A plastic charge is heated in the rheometer barrel and is forced through a die with a plunger. The plunger is pushed either by a constant force or at constant rate depending on the equipment. Measurements are taken once the system has reached steady-state operation. One method used is measuring Brookfield viscosity @ 140° C., units are mPa-s or cPoise, as known in the art. Alternatively, the melt viscosity can be measured using a rheometer, e.g. a commercially available AR-2000 Rheometer from Thermal Analysis Instruments, using the geometry of: 25 mm steel plate-standard steel parallel plate, and finding the plate over plate rheometry isotherm at 120° C., 0.01 hz shear rate. If the melt viscosity of a particular polymer is specified, unless otherwise stated, it is the melt viscosity for that polymer alone, in the absence of any of the other components of the electrostatic composition.

A certain monomer may be described herein as constituting a certain weight percentage of a polymer. This indicates that the repeating units formed from the said monomer in the polymer constitute said weight percentage of the polymer.

If a standard test is mentioned herein, unless otherwise stated, the version of the test to be referred to is the most recent at the time of filing this patent application.

As used herein, "electrostatic printing" or "electrophotographic printing" generally refers to the process that provides an image that is transferred from a photo imaging substrate either directly or indirectly via an intermediate transfer member to a print substrate. As such, the image is not substantially absorbed into the photo imaging substrate on which it is applied. Additionally, "electrophotographic printers" or "electrostatic printers" generally refer to those printers capable of performing electrophotographic printing or electrostatic printing, as described above. "Liquid electrophotographic printing" is a specific type of electrophotographic printing where a liquid composition is employed in the electrophotographic process rather than a powder toner. An electrostatic printing process may involve subjecting the electrostatic composition to an electric field, e.g. an electric field having a field gradient of 50-400V/μm, or more, ins some examples 600-900V/μm, or more.

As used herein, "substituted" may indicate that a hydrogen atom of a compound or moiety is replaced by another atom such as a carbon atom or a heteroatom, which is part of a group referred to as a substituent. Substituents include, for example, alkyl, alkoxy, aryl, aryloxy, alkenyl, alkenoxy, alkynyl, alkynoxy, thioalkyl, thioalkenyl, thioalkynyl, thioaryl, etc.

As used herein, "heteroatom" may refer to nitrogen, oxygen, halogens, phosphorus, or sulfur.

As used herein, "alkyl", or similar expressions such as "alk" in alkaryl, may refer to a branched, unbranched, or cyclic saturated hydrocarbon group, which may, in some examples, contain from 1 to about 50 carbon atoms, or 1 to about 40 carbon atoms, or 1 to about 30 carbon atoms, or 1 to about 10 carbon atoms, or 1 to about 5 carbon atoms for example.

The term "aryl" may refer to a group containing a single aromatic ring or multiple aromatic rings that are fused together, directly linked, or indirectly linked (such that the different aromatic rings are bound to a common group such as a methylene or ethylene moiety). Aryl groups described herein may contain, but are not limited to, from 5 to about 50 carbon atoms, or 5 to about 40 carbon atoms, or 5 to 30 carbon atoms or more, and may be selected from, phenyl and naphthyl.

As used herein, the term "about" is used to provide flexibility to a numerical range endpoint by providing that a given value may be a little above or a little below the endpoint to allow for variation in test methods or apparatus. The degree of flexibility of this term can be dictated by the particular variable and would be within the knowledge of those skilled in the art to determine based on experience and the associated description herein.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not just the numerical values explicitly recited as the limits of the range, but also to include all the individual numerical values or sub-ranges encompassed within that range as if each numerical value and sub-range is explicitly recited. As an illustration, a numerical range of "about 1 wt % to about 5 wt %" should be interpreted to include not just the explicitly recited values of about 1 wt % to about 5 wt %, but also include individual values and subranges within the indicated range. Thus, included in this numerical range are individual values such as 2, 3.5, and 4 and sub-ranges such as from 1-3, from 2-4, and from 3-5, etc. This same principle applies to ranges reciting a single numerical value. Furthermore, such an interpretation should apply regardless of the breadth of the range or the characteristics being described.

As used herein, wt % values are to be taken as referring to a weight-for-weight (w/w) percentage of solids in the composition, and not including the weight of any carrier fluid present.

In an aspect, there is provided a method for the manufacture of a charge director comprising a barium salt, said method comprising:
  reacting barium alkoxide with an acid in a reaction medium comprising ethanol, and
  separating ethanol from the reaction mixture to recover the barium salt produced.

Barium alkoxides are soluble in ethanol and can react in an ethanolic solution of acid to produce barium salt. The barium salt may then be separated from the reaction mixture, for example, by distillation of the ethanol. In known methods, barium hydroxide is reacted with acid. Barium hydroxide typically contains barium carbonate impurities, which are generally removed by dissolving the barium hydroxide in a solvent and separating the insoluble carbonates by filtration. Barium hydroxide, however, is not soluble in ethanol but soluble in methanol. Accordingly, it is typically dissolved in methanol and the resulting solution is reacted with the acid in the ethanolic reaction medium. The barium salt produced, however, must be separated from a mixture of ethanol and methanol. Because of their closeness in boiling point, methanol and ethanol cannot be conveniently separated from one another by distillation, making recycling of the solvents impossible. Furthermore, traces of methanol may be found in the final product. This may be undesirable, for example, from an environmental standpoint.

By replacing barium hydroxide with barium alkoxide, such as barium ethoxide, it is possible to produce the barium salt charge director in the absence of methanol. The reaction between the barium alkoxide and acid can take place in an ethanolic reaction medium without the need for methanol to dissolve the starting barium starting material. As the reaction mixture may be devoid of methanol, the ethanol in the reaction mixture may be separated and recycled. This improves the process, for example, from a cost and environmental standpoint. Furthermore, because barium alkoxide has a higher solubility in ethanol than barium hydroxide in methanol, the volume of solvent employed may be reduced. Moreover, because barium alkoxides can be sourced in a relatively pure form, it is not generally necessary to remove impurities, such as barium carbonate, from the starting material. This may allow the process to be carried out using the sourced starting material, without the need for (e.g. substantial) product purification and analysis prior to the reaction with acid.

In one example, the barium alkoxide is an alkoxide having 2 to 6, for instance, 2 to 4, carbon atoms. In one example, the barium alkoxide is barium ethoxide. Other examples include barium iso-propoxide.

The reaction between barium alkoxide and acid may occur in a reaction medium that contains less than 10 weight %, for example, less than 5 weight % methanol. The reaction medium may contain less than 1 weight % methanol. In one example, the reaction between barium alkoxide with an acid occurs in the substantial absence of methanol.

The acid may be any suitable acid. In one example, the acid is an inorganic acid and/or an organic acid. Examples of suitable organic acids include those based on sulfosuccinic acid. For example, the organic acid may comprise a sulfosuccinic acid alkyl or dialkyl ester. In one example, the acid is selected from at least one of a sulfosuccinic acid dialkyl ester and phosphoric acid. The acid may comprise both a sulfosuccinic acid dialkyl ester and phosphoric acid. The sulfosuccinic acid may be a sulfosuccinic acid di-alkyl ester. The alkyl groups of the sulfosuccinic acid (di-)alkyl ester may be a $C_3$ to $C_{30}$ alkyl, for example, a $C_{10}$ to $C_{20}$ alkyl. In one example, the alkyl groups may be a $C_{11}$ to $C_{15}$ group, for instance, $C_{13}$ alkyl. In the dialkyl ester, both alkyl groups may be the same or different. The alkyl groups may be linear, cyclic or branched. In one example, the acid comprises a sulfosuccinic acid ditridecyl (e.g. $C_{13}H_{27}$) ester and phosphoric acid.

In one example, the acid comprises a 2-sulfosuccinic acid dialkyl ester optionally in combination with phosphoric acid. The 2-sulfosuccinic acid dialkyl ester may have the formula below:

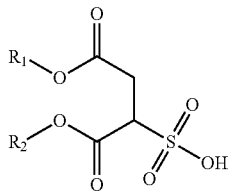

where $R_1$ and $R_2$ are each alkyl, for example, independently selected from $C_3$ to $C_{30}$ alkyl. $R_1$ and $R_2$ may be the same or different. In one example, $R_1$ and $R_2$ may each be selected from $C_{10}$ to $C_{20}$ alkyl or $C_{11}$ to $C_{15}$ alkyl. In another example, $R_1$ and $R_2$ are both $C_{13}$ alkyl (e.g. $C_{13}H_{27}$). The alkyl group may be linear or branched.

In one example, the barium salt produced has a reverse micelle structure. For instance, the barium salt may comprise nanoparticles of an inorganic barium salt and a barium salt of a sulfosuccinic acid di-alkyl ester. The barium salt of the sulfosuccinic acid di-alkyl ester may form micelles around the nanoparticles of the inorganic barium salt. In one example, the barium salt produced comprises barium hydrogenphosphate and a barium salt of a sulfosuccinic acid di-alkyl ester, for example, the barium salt of a sulfosuccinic acid di-alkyl ester as described above (e.g. the barium salt of a sulfosuccinic acid ditridecyl ester).

In one example, the sulfosuccinic acid alkyl ester is provided as an ethanolic solution by dissolving an alkali metal (e.g. sodium salt) of the sulfosuccinic acid alkyl (e.g. di-alkyl) ester in a first organic solvent,
  adding aqueous acid to the solution to form the sulfosuccinic acid alkyl ester and sodium salt of the acid,
  removing the sodium salt of the acid as an aqueous phase to leave an organic phase comprising the sulfosuccinic acid alkyl ester in the first organic solvent,
  extracting the sulfosuccinic acid alkyl ester from the first organic solvent by adding a second organic solvent to the organic phase,
  removing the first organic solvent from the organic phase, for example, by distillation, and
  adding ethanol to the organic phase to dissolve or extract the sulfosuccinic acid alkyl ester as an ethanolic solution of the sulfosuccinic acid alkyl ester.

As mentioned above, the alkali metal (e.g. sodium salt) of the sulfosuccinic acid alkyl (e.g. di-alkyl) ester may be dissolved in a first organic solvent. The first organic solvent may be any suitable organic solvent, for example, methyl t-butyl ether (MTBE). The salt may then be acidified by addition of an aqueous solution of an acid, for example, sulphuric acid. The alkali metal salt produced (e.g. sodium sulphate) is removed as an aqueous phase, while the sulfosuccinic acid alkyl ester is retained as an organic phase comprising the first organic solvent. The sulfosuccinic acid alkyl ester is then extracted from the first organic solvent into a second organic solvent by adding the second organic solvent to the organic phase. The second organic solvent may be any suitable non-polar solvent, including paraffinic solvents (e.g. Isopar™). The first organic solvent may then be removed, for example, by distillation. Once distilled, the content of non-volatile solids in the solution of sulfosuccinic acid alkyl ester in the second organic solvent (e.g. paraffinic solvent) may be at least 20%, for example, 20 to 50%.

Ethanol and, for example, phosphoric acid may then be added to the sulfosuccinic acid alkyl ester dissolved second organic solvent. The barium alkoxide may then be added drop wise, for example, as an ethanolic solution. The barium alkoxide reacts with the sulfosuccinic acid alkyl ester to produce a barium salt of the sulfosuccinic acid alkyl ester. For instance, an illustrative example of the reaction between the barium alkoxide and the sulfosuccinic acid alkyl ester is as follows:

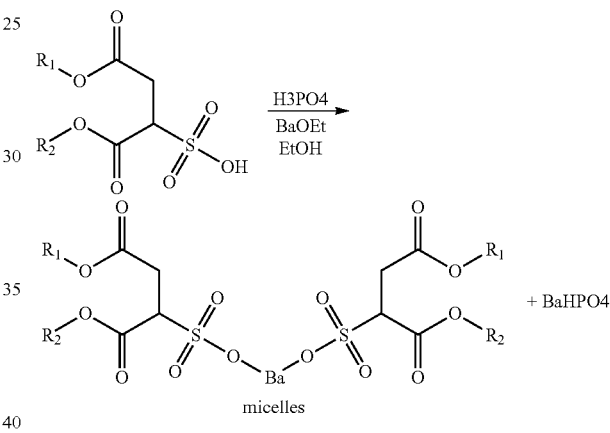

where $R_1$ and $R_2$ are as defined above, for example, each $C_{13}$ alkyl.

The barium salt produced may be recovered, for example, by distillation of the ethanol. This may leave a solution of the barium salt in the second organic solvent (e.g. paraffinic solvent (Isopar™)). The non-volatile solids content of this solution may be at least 15%, for example, 20-60%, for example, about 30%.

The ethanol that is distilled may be recovered and recycled for re-use. In some examples, additional amounts of the second organic solvent (e.g. paraffinic solvent (Isopar™)) are not added after distillation of the ethanol.

The barium salt produced in the method described herein is suitable for use as a charge director in a liquid electrophotographic ink or varnish composition. A charge director is suitable for imparting a charge of a desired polarity and/or maintain sufficient electrostatic charge on the particles of an electrostatic composition. As explained above, the barium salt in some examples includes an inorganic barium salt and a barium salt of an alkyl sulfosuccinic acid. The latter may form micelles around, for example, nanoparticles of the former in, for instance, a reverse micelle structure.

In one example, the method further includes using the barium salt produced in a liquid electrophotographic ink or varnish composition. For example, the barium salt may be added to a liquid electrophotographic ink or varnish composition comprising an acid polymer, a charge adjuvant, a carrier liquid and optionally a colorant.

Charge Director

As described above, the barium salt produced in the method described herein can comprise a barium salt of sulfosuccinic acid di alkyl ester of the formula:

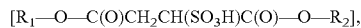

[R₁—O—C(O)CH₂CH(SO₃H)C(O)—O—R₂], where each of $R_1$ and $R_2$ are alkyl groups, for example, linear, branched or cyclic alkyl groups.

In some examples, the charge director comprises nanoparticles of a simple salt and a salt of the general formula $MA_n$, wherein M is a barium, n is 2, and A is an ion of the general formula [R₁—O—C(O)CH₂CH(SO₃⁻)C(O)—O—R₂], where each of $R_1$ and $R_2$ is an alkyl group e.g. as discussed above.

The sulfosuccinate salt of the general formula $MA_n$ is an example of a micelle forming salt. The charge director may be substantially free or free of an acid of the general formula HA, where A is as described above. The charge director may comprise micelles of said sulfosuccinate salt enclosing at least some of the nanoparticles. The charge director may comprise at least some nanoparticles having a size of 10 nm or less, in some examples 2 nm or more (e.g. 4-6 nm).

The simple salt may comprise a cation selected from Mg, Ca, Ba, NH₄, tert-butyl ammonium, Li⁺, and Al⁺³, or from any sub-group thereof. In one example, the simple salt is an inorganic salt, for instance, a barium salt. The simple salt may comprise an anion selected from $SO_4^{2-}$, $PO^{3-}$, $NO_3^-$, $HPO_4^{2-}$, $CO_3^{2-}$, acetate, trifluoroacetate (TFA), Cl⁻, Bf, F⁻, $ClO_4^-$, and $TiO_3^{4-}$, or from any sub-group thereof. In some examples, the simple salt comprises a hydrogen phosphate anion.

The simple salt may be selected from CaCO₃, Ba₂TiO₃, Al₂(SO₄), Al(NO₃)₃, Ca₃(PO₄)₂, BaSO₄, BaHPO₄, Ba₂(PO₄)₃, CaSO₄, (NH₄)₂CO₃, (NH₄)₂SO₄, NH₄OAc, Tert-butyl ammonium bromide, NH₄NO₃, LiTFA, Al₂(SO₄)₃, LiClO₄ and LiBF₄, or any sub-group thereof. In one example, the simple salt may be BaHPO₄.

In the formula [R₁—O—C(O)CH₂CH(SO₃⁻)C(O)—O—R₂], in some examples, each of $R_1$ and $R_2$ is an aliphatic alkyl group. In some examples, each of $R_1$ and $R_2$ independently is a $C_{6-25}$ alkyl. In some examples, said aliphatic alkyl group is linear. In some examples, said aliphatic alkyl group is branched. In some examples, said aliphatic alkyl group includes a linear chain of more than 6 carbon atoms. In some examples, $R_1$ and $R_2$ are the same. In some examples, at least one of $R_1$ and $R_2$ is $C_{13}H_{27}$.

In an electrostatic composition, the charge director can constitute about 0.001% to 20%, in some examples 0.01 to 20% by weight, in some examples 0.01 to 10% by weight, in some examples 0.01 to 1% by weight of the solids of the electrostatic composition. The charge director can constitute about 0.001 to 0.15% by weight of the solids of the liquid electrophotographic composition, in some examples 0.001 to 0.15%, in some examples 0.001 to 0.02% by weight of the solids of the liquid electrophotographic composition. In some examples, the charge director imparts a negative charge on the electrostatic composition. The particle conductivity may range from 50 to 500 pmho/cm, in some examples from 200-350 pmho/cm.

Charge Adjuvant

The liquid electrophotographic composition can include a charge adjuvant. A charge adjuvant may be present with a charge director, and may be different to the charge director, and act to increase and/or stabilise the charge on particles, e.g. resin-containing particles, of an electrostatic composition. The charge adjuvant can include, but is not limited to, barium petronate, calcium petronate, Co salts of naphthenic acid, Ca salts of naphthenic acid, Cu salts of naphthenic acid, Mn salts of naphthenic acid, Ni salts of naphthenic acid, Zn salts of naphthenic acid, Fe salts of naphthenic acid, Ba salts of stearic acid, Co salts of stearic acid, Pb salts of stearic acid, Zn salts of stearic acid, Al salts of stearic acid, Cu salts of stearic acid, Fe salts of stearic acid, metal carboxylates (e.g. Al tristearate, Al octanoate, Li heptanoate, Fe stearate, Fe distearate, Ba stearate, Cr stearate, Mg octanoate, Ca stearate, Fe naphthenate, Zn naphthenate, Mn heptanoate, Zn heptanoate, Ba octanoate, Al octanoate, Co octanoate, Mn octanoate, and Zn octanoate), Co lineolates, Mn lineolates, Pb lineolates, Zn lineolates, Ca oleates, Co oleates, Zn palmirate, Ca resinates, Co resinates, Mn resinates, Pb resinates, Zn resinates, AB diblock co-polymers of 2-ethylhexyl methacrylate-co-methacrylic acid calcium, and ammonium salts, co-polymers of an alkyl acrylamidoglycolate alkyl ether (e.g. methyl acrylamidoglycolate methyl ether-co-vinyl acetate), and hydroxy bis(3,5-di-tert-butyl salicylic) aluminate monohydrate. In some examples, the charge adjuvant is aluminium di and/or tristearate and/or aluminium di and/or tripalmitate.

The charge adjuvant can constitute about 0.1 to 5% by weight of the solids of the liquid electrophotographic composition. The charge adjuvant can constitute about 0.5 to 4% by weight of the solids of the liquid electrophotographic composition. The charge adjuvant can constitute about 1 to 3% by weight of the solids of the liquid electrophotographic composition.

Carrier Liquid

Generally, the carrier liquid for the liquid electrophotographic composition can act as a dispersing medium for the other components in the electrostatic composition. For example, the carrier liquid can comprise or be a hydrocarbon, silicone oil, vegetable oil, etc. The carrier liquid can include, but is not limited to, an insulating, non-polar, non-aqueous liquid that can be used as a medium for toner particles. The carrier liquid can include compounds that have a resistivity in excess of about $10^9$ ohm-cm. The carrier liquid may have a dielectric constant below about 5, in some examples below about 3. The carrier liquid can include, but is not limited to, hydrocarbons. The hydrocarbon can include, but is not limited to, an aliphatic hydrocarbon, an isomerized aliphatic hydrocarbon, branched chain aliphatic hydrocarbons, aromatic hydrocarbons, and combinations thereof. Examples of the carrier liquids include, but are not limited to, aliphatic hydrocarbons, isoparaffinic compounds, paraffinic compounds, dearomatized hydrocarbon compounds, and the like. In particular, the carrier liquids can include, but are not limited to, Isopar-G™, Isopar-H™, Isopar-L™, Isopar-M™, Isopar-K™, Isopar-V™, Norpar 12™, Norpar 13™, Norpar 15™, Exxol D40™, Exxol D80™, Exxol D100™, Exxol D130™, and Exxol D140™ (each sold by EXXON CORPORATION); Teclen N-16™, Teclen N-20™, Teclen N-22™, Nisseki Naphthesol L™, Nisseki Naphthesol M™, Nisseki Naphthesol H™, #0 Solvent L™, #0 Solvent M™, #0 Solvent H™, Nisseki Isosol 300™, Nisseki Isosol 400™, AF-4™, AF-5™, AF-6™ and AF-7™ (each sold by NIPPON OIL CORPORATION); IP Solvent 1620™ and IP Solvent 2028™ (each sold by IDEMITSU PETROCHEMICAL CO., LTD.); Amsco OMS™ and Amsco 460™ (each sold by AMERICAN MINERAL SPIRITS CORP.); and Electron, Positron, New II, Purogen HF (100% synthetic terpenes) (sold by ECOLINK™).

Before printing, the carrier liquid can constitute about 20% to 99.5% by weight of the electrostatic composition, in some examples 50% to 99.5% by weight of the electrostatic composition. Before printing, the carrier liquid may constitute about 40 to 90% by weight of the electrostatic composition. Before printing, the carrier liquid may constitute about 60% to 80% by weight of the electrostatic composition. Before printing, the carrier liquid may constitute about 90% to 99.5% by weight of the electrostatic composition, in some examples 95% to 99% by weight of the electrostatic composition.

The ink, when printed on the print substrate, may be substantially free from carrier liquid. In an electrostatic printing process and/or afterwards, the carrier liquid may be removed, e.g. by an electrophoresis processes during printing and/or evaporation, such that substantially just solids are transferred to the print substrate. Substantially free from carrier liquid may indicate that the ink printed on the print substrate contains less than 5 wt % carrier liquid, in some examples, less than 2 wt % carrier liquid, in some examples less than 1 wt % carrier liquid, in some examples less than 0.5 wt % carrier liquid. In some examples, the ink printed on the print substrate is free from carrier liquid.

Polymer Resin

The composition can comprise a polymer resin. The polymer resin may comprise a thermoplastic polymer. A thermoplastic polymer is sometimes referred to as a thermoplastic resin. In one example, the polymer is a polymer of an alkylene (e.g. ethylene) and at least one of methacrylic acid or acrylic acid. In some examples, the polymer may be selected from ethylene or propylene acrylic acid co-polymers; ethylene or propylene methacrylic acid co-polymers; ethylene vinyl acetate co-polymers; co-polymers of ethylene or propylene (e.g. 80 wt % to 99.9 wt %), and alkyl (e.g. C1 to C5) ester of methacrylic or acrylic acid (e.g. 0.1 wt % to 20 wt %); co-polymers of ethylene (e.g. 80 wt % to 99.9 wt %), acrylic or methacrylic acid (e.g. 0.1 wt % to 20.0 wt %) and alkyl (e.g. C1 to C5) ester of methacrylic or acrylic acid (e.g. 0.1 wt % to 20 wt %); co-polymers of ethylene or propylene (e.g. 70 wt % to 99.9 wt %) and maleic anhydride (e.g. 0.1 wt % to 30 wt %); polyethylene; polystyrene; isotactic polypropylene (crystalline); co-polymers of ethylene ethylene ethyl acrylate; polyesters; polyvinyl toluene; polyamides; styrene/butadiene co-polymers; epoxy resins; acrylic resins (e.g. co-polymer of acrylic or methacrylic acid and at least one alkyl ester of acrylic or methacrylic acid wherein alkyl may have from 1 to about 20 carbon atoms, such as methyl methacrylate (e.g. 50% to 90%)/methacrylic acid (e.g. 0 wt % to 20 wt %)/ethylhexylacrylate (e.g. 10 wt % to 50 wt %)); ethylene-acrylate terpolymers: ethylene-acrylic esters-maleic anhydride (MAH) or glycidyl methacrylate (GMA) terpolymers; ethylene-acrylic acid ionomers and combinations thereof.

The resin may comprise a polymer having acidic side groups. Examples of the polymer having acidic side groups will now be described. The polymer having acidic side groups may have an acidity of 50 mg KOH/g or more, in some examples an acidity of 60 mg KOH/g or more, in some examples an acidity of 70 mg KOH/g or more, in some examples an acidity of 80 mg KOH/g or more, in some examples an acidity of 90 mg KOH/g or more, in some examples an acidity of 100 mg KOH/g or more, in some examples an acidity of 105 mg KOH/g or more, in some examples 110 mg KOH/g or more, in some examples 115 mg KOH/g or more. The polymer having acidic side groups may have an acidity of 200 mg KOH/g or less, in some examples 190 mg or less, in some examples 180 mg or less, in some examples 130 mg KOH/g or less, in some examples 120 mg KOH/g or less. Acidity of a polymer, as measured in mg KOH/g can be measured using standard procedures known in the art, for example using the procedure described in ASTM D1386.

The resin may comprise a polymer, in some examples a polymer having acidic side groups, that has a melt flow rate of less than about 70 g/10 minutes, in some examples about 60 g/10 minutes or less, in some examples about 50 g/10 minutes or less, in some examples about 40 g/10 minutes or less, in some examples 30 g/10 minutes or less, in some examples 20 g/10 minutes or less, in some examples 10 g/10 minutes or less. In some examples, all polymers having acidic side groups and/or ester groups in the particles each individually have a melt flow rate of less than 90 g/10 minutes, 80 g/10 minutes or less, in some examples 80 g/10 minutes or less, in some examples 70 g/10 minutes or less, in some examples 70 g/10 minutes or less, in some examples 60 g/10 minutes or less.

The polymer having acidic side groups can have a melt flow rate of about 10 g/10 minutes to about 120 g/10 minutes, in some examples about 10 g/10 minutes to about 70 g/10 minutes, in some examples about 10 g/10 minutes to 40 g/10 minutes, in some examples 20 g/10 minutes to 30 g/10 minutes. The polymer having acidic side groups can have a melt flow rate of, in some examples, about 50 g/10 minutes to about 120 g/10 minutes, in some examples 60 g/10 minutes to about 100 g/10 minutes. The melt flow rate can be measured using standard procedures known in the art, for example as described in ASTM D1238.

The acidic side groups may be in free acid form or may be in the form of an anion and associated with one or more counterions, typically metal counterions, e.g. a metal selected from the alkali metals, such as lithium, sodium and potassium, alkali earth metals, such as magnesium or calcium, and transition metals, such as zinc. The polymer having acidic sides groups can be selected from resins such as co-polymers of ethylene and an ethylenically unsaturated acid of either acrylic acid or methacrylic acid; and ionomers thereof, such as methacrylic acid and ethylene-acrylic or methacrylic acid co-polymers which are at least partially neutralized with metal ions (e.g. Zn, Na, Li) such as SUR-LYN® ionomers. The polymer comprising acidic side groups can be a co-polymer of ethylene and an ethylenically unsaturated acid of either acrylic or methacrylic acid, where the ethylenically unsaturated acid of either acrylic or methacrylic acid constitute from 5 wt % to about 25 wt % of the co-polymer, in some examples from 10 wt % to about 20 wt % of the co-polymer.

The resin may comprise two different polymers having acidic side groups. The two polymers having acidic side groups may have different acidities, which may fall within the ranges mentioned above. The resin may comprise a first polymer having acidic side groups that has an acidity of from 10 mg KOH/g to 110 mg KOH/g, in some examples 20 mg KOH/g to 110 mg KOH/g, in some examples 30 mg KOH/g to 110 mg KOH/g, in some examples 50 mg KOH/g to 110 mg KOH/g, and a second polymer having acidic side groups that has an acidity of 110 mg KOH/g to 130 mg KOH/g.

The resin may comprise two different polymers having acidic side groups: a first polymer having acidic side groups that has a melt flow rate of about 10 g/10 minutes to about 50 g/10 minutes and an acidity of from 10 mg KOH/g to 110 mg KOH/g, in some examples 20 mg KOH/g to 110 mg KOH/g, in some examples 30 mg KOH/g to 110 mg KOH/g, in some examples 50 mg KOH/g to 110 mg KOH/g, and a second polymer having acidic side groups that has a melt flow rate of about 50 g/10 minutes to about 120 g/10 minutes and an acidity of 110 mg KOH/g to 130 mg KOH/g. The first and second polymers may be absent of ester groups.

The ratio of the first polymer having acidic side groups to the second polymer having acidic side groups can be from about 10:1 to about 2:1. The ratio can be from about 6:1 to about 3:1, in some examples about 4:1.

The resin may comprise a polymer having a melt viscosity of 15000 poise or less, in some examples a melt viscosity of 10000 poise or less, in some examples 1000 poise or less, in some examples 100 poise or less, in some examples 50 poise or less, in some examples 10 poise or less; said polymer may be a polymer having acidic side groups as described herein. The resin may comprise a first polymer having a melt viscosity of 15000 poise or more, in some examples 20000 poise or more, in some examples 50000 poise or more, in some examples 70000 poise or more; and in some examples, the resin may comprise a second polymer having a melt viscosity less than the first polymer, in some examples a melt viscosity of 15000 poise or less, in some examples a melt viscosity of 10000 poise or less, in some examples 1000 poise or less, in some examples 100 poise or less, in some examples 50 poise or less, in some examples 10 poise or less. The resin may comprise a first polymer having a melt viscosity of more than 60000 poise, in some examples from 60000 poise to 100000 poise, in some examples from 65000 poise to 85000 poise; a second polymer having a melt viscosity of from 15000 poise to 40000 poise, in some examples 20000 poise to 30000 poise, and a third polymer having a melt viscosity of 15000 poise or less, in some examples a melt viscosity of 10000 poise or less, in some examples 1000 poise or less, in some examples 100 poise or less, in some examples 50 poise or less, in some examples 10 poise or less; an example of the first polymer is Nucrel 960 (from DuPont), and example of the second polymer is Nucrel 699 (from DuPont), and an example of the third polymer is AC-5120 or AC-5180 (from Honeywell). The first, second and third polymers may be polymers having acidic side groups as described herein. The melt viscosity can be measured using a rheometer, e.g. a commercially available AR-2000 Rheometer from Thermal Analysis Instruments, using the geometry of: 25 mm steel plate-standard steel parallel plate, and finding the plate over plate rheometry isotherm at 120° C., 0.01 hz shear rate.

If the resin in the electrophotographic composition comprises a single type of polymer, the polymer (excluding any other components of the electrostatic composition) may have a melt viscosity of 6000 poise or more, in some examples a melt viscosity of 8000 poise or more, in some examples a melt viscosity of 10000 poise or more, in some examples a melt viscosity of 12000 poise or more. If the resin comprises a plurality of polymers all the polymers of the resin may together form a mixture (excluding any other components of the electrostatic composition) that has a melt viscosity of 6000 poise or more, in some examples a melt viscosity of 8000 poise or more, in some examples a melt viscosity of 10000 poise or more, in some examples a melt viscosity of 12000 poise or more. Melt viscosity can be measured using standard techniques. The melt viscosity can be measured using a rheometer, e.g. a commercially available AR-2000 Rheometer from Thermal Analysis Instruments, using the geometry of: 25 mm steel plate-standard steel parallel plate, and finding the plate over plate rheometry isotherm at 120° C., 0.01 hz shear rate.

The resin may comprise two different polymers having acidic side groups that are selected from co-polymers of ethylene and an ethylenically unsaturated acid of either acrylic acid or methacrylic acid; or ionomers thereof, such as methacrylic acid and ethylene-acrylic or methacrylic acid co-polymers which are at least partially neutralized with metal ions (e.g. Zn, Na, Li) such as SURLYN® ionomers. The resin may comprise (i) a first polymer that is a co-polymer of ethylene and an ethylenically unsaturated acid of either acrylic acid and methacrylic acid, wherein the ethylenically unsaturated acid of either acrylic or methacrylic acid constitutes from 8 wt % to about 16 wt % of the co-polymer, in some examples 10 wt % to 16 wt % of the co-polymer; and (ii) a second polymer that is a co-polymer of ethylene and an ethylenically unsaturated acid of either acrylic acid and methacrylic acid, wherein the ethylenically unsaturated acid of either acrylic or methacrylic acid constitutes from 12 wt % to about 30 wt % of the co-polymer, in some examples from 14 wt % to about 20 wt % of the co-polymer, in some examples from 16 wt % to about 20 wt % of the co-polymer in some examples from 17 wt % to 19 wt % of the co-polymer.

The resin may comprise a polymer having acidic side groups, as described above (which may be free of ester side groups), and a polymer having ester side groups. The polymer having ester side groups may be a thermoplastic polymer. The polymer having ester side groups may further comprise acidic side groups. The polymer having ester side groups may be a co-polymer of a monomer having ester side groups and a monomer having acidic side groups. The polymer may be a co-polymer of a monomer having ester side groups, a monomer having acidic side groups, and a monomer absent of any acidic and ester side groups. The monomer having ester side groups may be a monomer selected from esterified acrylic acid or esterified methacrylic acid. The monomer having acidic side groups may be a monomer selected from acrylic or methacrylic acid. The monomer absent of any acidic and ester side groups may be an alkylene monomer, including, but not limited to, ethylene or propylene. The esterified acrylic acid or esterified methacrylic acid may, respectively, be an alkyl ester of acrylic acid or an alkyl ester of methacrylic acid. The alkyl group in the alkyl ester of acrylic or methacrylic acid may be an alkyl group having 1 to 30 carbons, in some examples 1 to 20 carbons, in some examples 1 to 10 carbons; in some examples selected from methyl, ethyl, iso-propyl, n-propyl, t-butyl, iso-butyl, n-butyl and pentyl.

The polymer having ester side groups may be a co-polymer of a first monomer having ester side groups, a second monomer having acidic side groups and a third monomer which is an alkylene monomer absent of any acidic and ester side groups. The polymer having ester side groups may be a co-polymer of (i) a first monomer having ester side groups selected from esterified acrylic acid or esterified methacrylic acid, in some examples an alkyl ester of acrylic or methacrylic acid, (ii) a second monomer having acidic side groups selected from acrylic or methacrylic acid and (iii) a third monomer which is an alkylene monomer selected from ethylene and propylene. The first monomer may constitute 1% to 50% by weight of the co-polymer, in some examples 5% to 40% by weight, in some examples 5% to 20% by weight of the co-polymer, in some examples 5% to 15% by weight of the co-polymer. The second monomer may constitute 1% to 50% by weight of the co-polymer, in some examples 5% to 40% by weight of the co-polymer, in some examples 5% to 20% by weight of the co-polymer, in some examples 5% to 15% by weight of the co-polymer. The first monomer can constitute 5% to 40% by weight of the co-polymer, the second monomer constitutes 5% to 40% by weight of the co-polymer, and with the third monomer constituting the remaining weight of the co-polymer. In some examples, the first monomer constitutes 5% to 15% by weight of the co-polymer, the second monomer constitutes 5% to 15% by weight of the co-polymer, with the third monomer constituting the remaining weight of the co-polymer. In some examples, the first monomer constitutes 8% to 12% by weight of the co-polymer, the second monomer constitutes 8% to 12% by weight of the co-polymer, with the third monomer constituting the remaining weight of the co-polymer. In some examples, the first monomer constitutes about 10% by weight of the co-polymer, the second monomer constitutes about 10% by weight of the co-polymer, and with the third monomer constituting the remaining weight of the co-polymer. The polymer may be selected from the Bynel® class of monomer, including Bynel 2022 and Bynel 2002, which are available from DuPont®.

The polymer having ester side groups may constitute 1% or more by weight of the total amount of the resin polymers, e.g. thermoplastic resin polymers, in the liquid electrophotographic composition, e.g. the total amount of the polymer or polymers having acidic side groups and polymer having ester side groups. The polymer having ester side groups may constitute 5% or more by weight of the total amount of the resin polymers, e.g. thermoplastic resin polymers, in some examples 8% or more by weight of the total amount of the resin polymers, e.g. thermoplastic resin polymers, in some examples 10% or more by weight of the total amount of the resin polymers, e.g. thermoplastic resin polymers, in some examples 15% or more by weight of the total amount of the resin polymers, e.g. thermoplastic resin polymers, in some examples 20% or more by weight of the total amount of the resin polymers, e.g. thermoplastic resin polymers, in some examples 25% or more by weight of the total amount of the resin polymers, e.g. thermoplastic resin polymers, in some examples 30% or more by weight of the total amount of the resin polymers, e.g. thermoplastic resin polymers, in some examples 35% or more by weight of the total amount of the resin polymers, e.g. thermoplastic resin polymers, in the liquid electrophotographic composition. The polymer having ester side groups may constitute from 5% to 50% by weight of the total amount of the resin polymers, e.g. thermoplastic resin polymers, in the liquid electrophotographic composition, in some examples 10% to 40% by weight of the total amount of the resin polymers, e.g. thermoplastic resin polymers, in the liquid electrophotographic composition, in some examples 5% to 30% by weight of the total amount of the resin polymers, e.g. thermoplastic resin polymers, in the liquid electrophotographic composition, in some examples 5% to 15% by weight of the total amount of the resin polymers, e.g. thermoplastic resin polymers, in the liquid electrophotographic composition in some examples 15% to 30% by weight of the total amount of the resin polymers, e.g. thermoplastic resin polymers, in the liquid electrophotographic composition.

The polymer having ester side groups may have an acidity of 50 mg KOH/g or more, in some examples an acidity of 60 mg KOH/g or more, in some examples an acidity of 70 mg KOH/g or more, in some examples an acidity of 80 mg KOH/g or more. The polymer having ester side groups may have an acidity of 100 mg KOH/g or less, in some examples 90 mg KOH/g or less. The polymer having ester side groups may have an acidity of 60 mg KOH/g to 90 mg KOH/g, in some examples 70 mg KOH/g to 80 mg KOH/g.

The polymer having ester side groups may have a melt flow rate of about 10 g/10 minutes to about 120 g/10 minutes, in some examples about 10 g/10 minutes to about 50 g/10 minutes, in some examples about 20 g/10 minutes to about 40 g/10 minutes, in some examples about 25 g/10 minutes to about 35 g/10 minutes.

The polymer, polymers, co-polymer or co-polymers of the resin can in some examples be selected from the Nucrel family of toners (e.g. Nucrel 403™, Nucrel 407™, Nucrel 609HS™, Nucrel 908HS™, Nucrel 1202HC™, Nucrel 30707™, Nucrel 1214™, Nucrel 903™, Nucrel 3990™, Nucrel 910™, Nucrel 925™, Nucrel 699™, Nucrel 599™, Nucrel 960™, Nucrel RX 76™, Nucrel 2806™, Bynell 2002, Bynell 2014, Bynell 2020 and Bynell 2022, (sold by E. I. du PONT)), the Aclyn family of toners (e.g. Aclyn 201, Aclyn 246, Aclyn 285, and Aclyn 295), and the Lotader family of toners (e.g. Lotader 2210, Lotader, 3430, and Lotader 8200 (sold by Arkema)).

The resin can constitute about 5 to 90%, in some examples about 50 to 80%, by weight of the solids of the liquid electrophotographic composition. The resin can constitute about 60 to 95%, in some examples about 70 to 95%, by weight of the solids of the liquid electrophotographic composition.

Colorants

The electrophotographic composition and/or ink printed on the print substrate may further include a colorant. The colorant may be selected from a pigment, dye and a combination thereof. The colorant may be transparent, unicolor or composed of any combination of available colors. The colorant may be selected from a cyan colorant, a yellow colorant, a magenta colorant and a black colorant. The electrophotographic composition and/or ink printed on the print substrate may include a plurality of colorants. The electrophotographic composition and/or ink printed on the print substrate may include a first colorant and second colorant, which are different from one another. Further colorants may also be present with the first and second colorants. The electrophotographic composition and/or ink printed on the print substrate may include first and second colorants where each is independently selected from a cyan colorant, a yellow colorant, a magenta colorant and a black colorant. In some examples, the first colorant includes a black colorant, and the second colorant includes a non-black colorant, for example a colorant selected from a cyan colorant, a yellow colorant and a magenta colorant. The colorant may be selected from a phthalocyanine colorant, an indigold colorant, an indanthrone colorant, a monoazo colorant, a diazo colorant, inorganic salts and complexes, dioxazine colorant, perylene colorant, anthraquinone colorants, and any combination thereof.

Printing Process and Print Substrate

In some examples, the liquid electrophotographic composition as described herein is printed onto a substrate using a liquid electrophotographic printer.

In some examples, the surface on which the image is formed or developed may be on a rotating member, e.g. in the form of a cylinder. The surface on which the printed image is formed or developed may form part of a photo imaging plate (PIP). The method may involve passing the composition between a stationary electrode and a rotating member, which may be a member having the surface having the (latent) electrostatic image thereon or a member in contact with the surface having the (latent) electrostatic image thereon. A voltage is applied between the stationary electrode and the rotating member, such that particles adhere to the surface of the rotating member. The intermediate transfer member, if present, may be a rotating flexible member, which may be heated, e.g. to a temperature of from 80 to 160° C.

The print substrate may be any suitable substrate. The substrate may be any suitable substrate capable of having an image printed thereon. The substrate may include a material selected from an organic or inorganic material. The material may include a natural polymeric material, e.g. cellulose. The material may include a synthetic polymeric material, e.g. a polymer formed from alkylene monomers, including, but not limited to, polyethylene and polypropylene, and co-polymers such as styrene-polybutadiene. The polypropylene may, in some examples, be biaxially orientated polypropylene. The material may include a metal, which may be in sheet form. The metal may be selected from or made from, for instance, aluminium (Al), silver (Ag), tin (Sn), copper (Cu), mixtures thereof. In an example, the substrate includes a cellulosic paper. In an example, the cellulosic paper is coated with a polymeric material, e.g. a polymer formed from styrene-butadiene resin. In some examples, the cellulosic paper has an inorganic material bound to its surface (before printing with ink) with a polymeric material, wherein the inorganic material may be selected from, for example, kaolinite or calcium carbonate. The substrate is, in some examples, a cellulosic print substrate such as paper. The cellulosic print substrate is, in some examples, a coated cellulosic print. In some examples, a primer may be coated onto the print substrate, before the electrostatic composition is printed onto the print substrate.

EXAMPLES

Comparative Example 1

In this example, a charge director comprising a barium salt is produced using the method shown in the flow diagram in FIG. 1.

Stage 1:

NaTR (or Na $[C_{13}H_{27}-O-C(O)CH_2CH(SO_3^-)C(O)-O-C_{13}H_{27}]$) is dissolved in methyl t-butyl ether (MTBE) and water. Then, aqueous $H_2SO_4$ is added drop wise to the mixture for 30 min to acidify the NaTR to form HTR (or $H[C_{13}H_{27}-O-C(O)CH_2CH(SO_3^-) C(O)-O-C_{13}H_{27}]$).

After H2SO4 addition, the mixture is stirred for 0.5 hr. Phase separation occurs to produce an MTBE phase containing the HTR, and an aquoeus phase containing $Na_2SO_4$. The aqueous phase is taking out to waste, while the HTR-containing MTBE phase is retained. Isopar is then added to the mixture and MTBE is removed by distillation. The HTR is now dissolved in Isopar.

Stage 2:

Ethanol and $H_3PO_4$ is then added to the HTR in Isopar. Barium hydroxide dissolved in methanol is then added drop wise (after it was filtered to remove carbonate impurities). The barium hydroxide reacts with both HTR and $H_3PO_4$ to produce Barium hydrogen phosphate and a barium salt of HTR.

Ethanol and Methanol are then evaporated to leave the barium salt of HTR dissolved in Isopar. Because of their closeness in boiling point, these solvents cannot be conveniently separated from one another by distillation. Accordingly, the mixture of ethanol and methanol distilled from the product mixture is discarded.

Example 2

In this example, the barium hydroxide is replaced with barium ethoxide. Stage 1 Comparative Example 1 above remains unaltered. However, in Stage 2, the volume of ethanol required is substantially reduced as less ethanol is required to facilitate the acid-base reaction with an ethanolic solution of barium ethoxide compared to with a methanolic solution of barium hydroxide. Furthermore, barium ethoxide is used in place of barium hydroxide. As barium ethoxide is soluble in ethanol, it is dissolved in ethanol rather than methanol. Furthermore, because barium ethoxide has a higher solubility in ethanol than barium hydroxide in methanol, the total volume of alcohol solvent employed is reduced relative to that used in Comparative Example 1.

Figure 2:
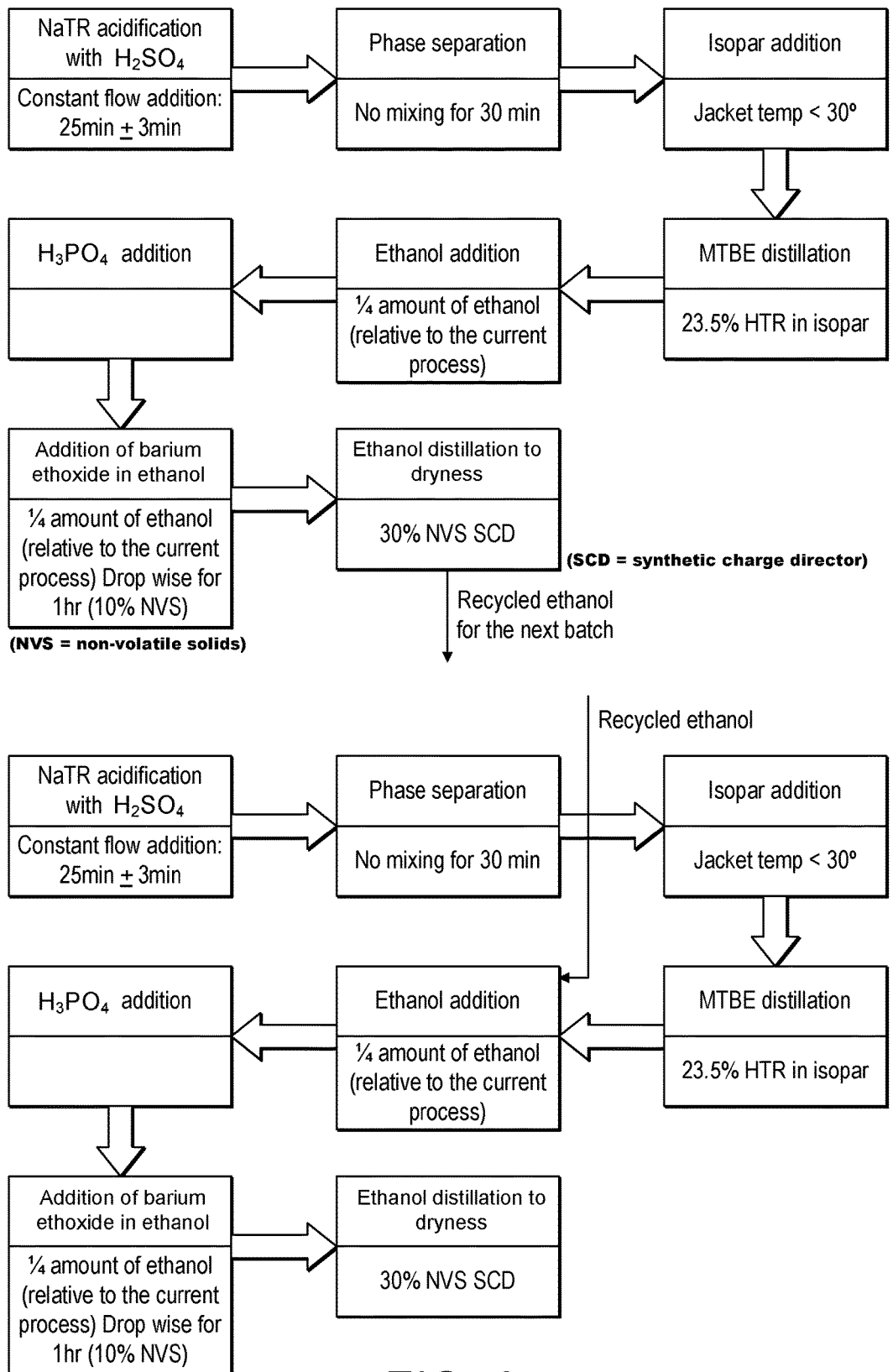
FIG. 2 is a schematic flow diagram of the method described in Example 2

Furthermore, because ethanol is employed in the absence of methanol, the ethanol produced can be separated by distillation and recycled for use in the manufacture of the subsequent batch. The flow diagram in FIG. 2 describes the process:

Based on 2000 L reactor scale, in the process of Comparative Example 1, the total amount of ethanol and methanol is 1470 Kg (420 Kg of Methanol and 1050 Kg of Ethanol).

In the process of Example 2, 210 Kg of ethanol (i.e. equivalent to 20% from the comparative process) is added after MTBE distillation and a second amount (210 kg) is added with the barium ethoxide salt. Accordingly, the total amount of ethanol used in the process of Example 2 is 420 Kg instead of 1050 Kg (60% reduction in ethanol amount). Because the process of Example 2 employs significantly less solvent that the process of Comparative Example 1, the reactor can be operated at a higher throughput of reactants. This can increase throughput by 250%. For example, in a 2000 L reactor, the amount of charge director produced per batch can potentially increase from 94 Kg to 240 Kg.

The table below shows the number of batches needed to be produced to produce 997.5 kg of charge director and 2700 kg of charge director, respectively, using 2000 l and 1000 l reactors, respectively. With the process of Example 2, it takes 4.2 and 11.3 batches using a 2000 L reactor to produce 997.5 kg and 2700 kg of product, respectively. In comparison, with the process of Comparative Example 1, it takes 10.4 and 28.1 batches to produce the same amounts of product using the same reactor. Similarly, with the process of Example 2, it takes 8.3 and 22.5 batches using a 1000 L reactor to produce 997.5 kg and 2700 kg of product, respectively. In comparison, it takes 21.2 and 57.4 batches using the same reactor to produce the same amounts of product.

| Year | Pure SCD (Kg) | No. of batches at 2000 L new process | No. of batches at 2000 L current process | No. of batches at 1000 L new process | No. of batches at 1000 L current process |
|---|---|---|---|---|---|
| 2017 | 997.5 | 4.2 | 10.4 | 8.3 | 21.2 |
| 2018 | 2700 | 11.3 | 28.1 | 22.5 | 57.4 |

Example 3

In this example, the charging efficacy of a charge director produced according to Example 2 was compared to a reference charge director produced according to Comparative Example 1 (SCD Reference). The tests were carried out using the same liquid electrophotographic cyan ink composition.

In this process, 4 different concentrations of a charge director produced according to Example 2 were added to the cyan ink. After incubation of the charge director with the ink for overnight, the HF value was tested in Q over M machine (to measure conductance of charge director in pmho/cm). The procedure was repeated with further batches of charge director produced according to the process of Example 2 (in total: R179, R191, R192). The observed curve is compared to the reference charge director in the aspect of curve trend and HF (high field conductivity) values.

Figure 3:
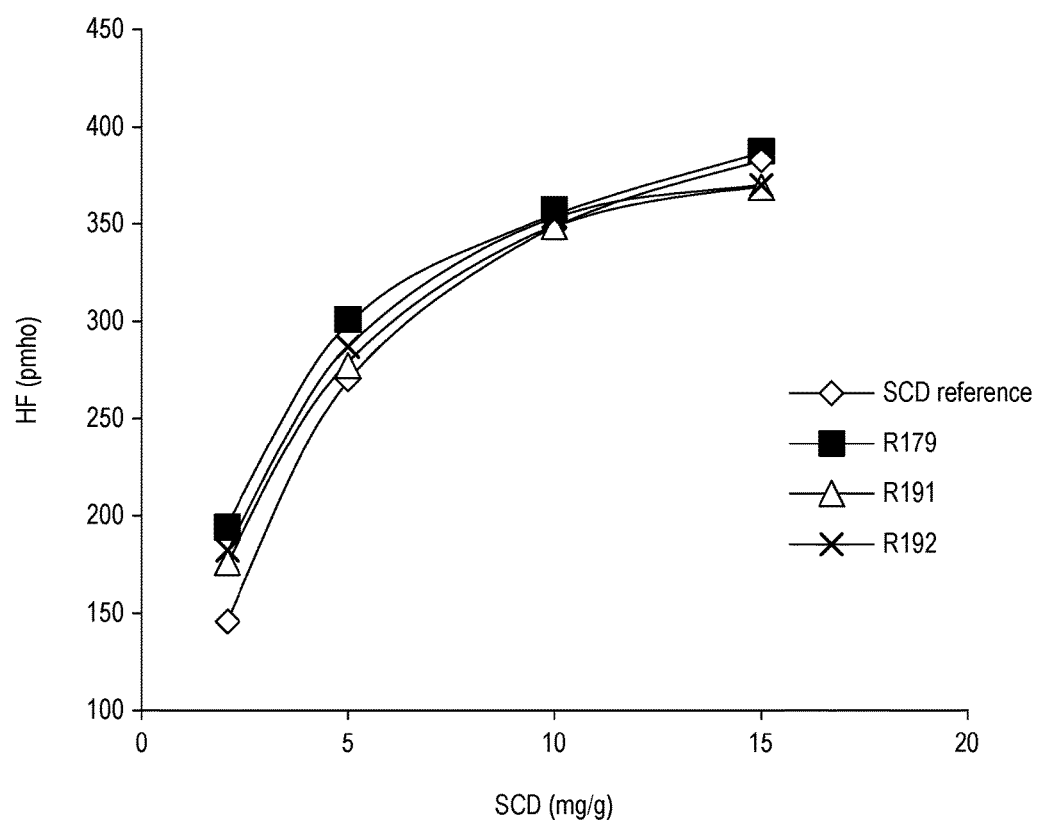
FIG. 3 shows the charging profile of a charge director formed according to Example 2.

As can be seen from FIG. 3, the charging profiles of the charge director produced according to process of Example 2 is substantially the same as that produced according to Comparative Example 1. This shows that a product of the same quality can be produced using a more cost effective, efficient and environmentally friendly process.

The invention claimed is:

1. A method for the manufacture of a charge director comprising a barium salt, said method comprising:
reacting barium alkoxide with an acid in a reaction medium comprising ethanol, wherein the reaction between barium alkoxide with the acid occurs in the substantial absence of methanol, and
separating ethanol from the reaction mixture to recover the barium salt produced.

2. A method as claimed in claim 1, wherein the barium alkoxide is barium ethoxide.

3. A method as claimed in claim 1, wherein the acid is selected from the group consisting of a sulfosuccinic acid alkyl ester, phosphoric acid, and a combination thereof.

4. A method as claimed in claim 3, wherein the acid is a combination of a sulfosuccinic acid alkyl ester and phosphoric acid.

5. A method as claimed in claim 3, wherein the sulfosuccinic acid alkyl ester is a sulfosuccinic acid dialkyl ester.

6. A method as claimed in claim 5, wherein the barium salt comprises barium hydrogenphosphate and a barium salt of a sulfosuccinic acid dialkyl ester.

7. A method as claimed in claim 6, wherein the barium salt of a sulfosuccinic acid dialkyl ester is a barium salt of:

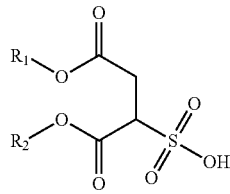

wherein $R_1$ and $R_2$ are each independently $C_{10}$ to $C_{20}$ alkyl groups.

8. A method as claimed in claim 3, wherein the sulfosuccinic acid is provided as an ethanolic solution by
dissolving an alkali metal salt of the sulfosuccinic acid alkyl ester in a first organic solvent,
adding aqueous sulphuric acid to the solution to form the sulfosuccinic acid alkyl ester and alkali metal sulphate,
removing alkali metal sulphate as an aqueous phase to leave an organic phase comprising the sulfosuccinic acid alkyl ester in the first organic solvent,
extracting the sulfosuccinic acid alkyl ester from the first organic solvent by adding a second organic solvent to the organic phase,
removing the first organic solvent from the organic phase by distillation, and
adding ethanol to the organic phase to extract the sulfosuccinic acid alkyl ester as an ethanolic solution of the sulfosuccinic acid alkyl ester.

9. A method as claimed in claim 8, wherein phosphoric acid is added to the ethanolic solution of the sulfosuccinic acid alkyl ester.

10. A method as claimed in claim 8, wherein the barium alkoxide is added to the ethanolic solution of the sulfosuccinic acid alkyl ester.

11. A method as claimed in claim 1, wherein the barium salt produced is recovered by distillation of the ethanol.

12. A method as claimed in claim 11, wherein the distilled ethanol is recycled for use as the reaction medium for the reaction between the barium alkoxide and acid.

13. A method as claimed in claim 1, which comprises using the barium salt produced in a liquid electrophotographic ink or varnish composition.

14. A method as claimed in claim 13, wherein the liquid electrophotographic ink or varnish composition is electrophotographically printed onto a substrate.

15. A method as claimed in claim 2, wherein the acid is selected from the group consisting of a sulfosuccinic acid alkyl ester, phosphoric acid, and a combination thereof.

16. A method as claimed in claim 2, wherein the acid comprises a sulfosuccinic acid alkyl ester and phosphoric acid.

17. A method as claimed in claim 1, wherein the acid comprises a sulfosuccinic acid alkyl ester and phosphoric acid.

* * * * *